United States Patent [19]

Nedelec et al.

[11] 4,435,408
[45] Mar. 6, 1984

[54] DOPAMINERGIC STIMULATING AND ANTIANOXIC 4-SUBSTITUTED 2H-INDOLE-2-ONES

[75] Inventors: Lucien Nedelec, Le Raincy; Jacques Guillaume, Le Pre Saint Gervais; Claude Dumont, Nogent sur Marne, all of France

[73] Assignee: Roussel Uclaf, Paris, France

[21] Appl. No.: 398,576

[22] Filed: Jul. 15, 1982

[30] Foreign Application Priority Data

Jul. 24, 1981 [FR] France .................. 81 14429

[51] Int. Cl.³ .................. A61K 31/44; A61K 31/445; C07D 401/04
[52] U.S. Cl. .................. 424/263; 424/267; 546/201; 546/273
[58] Field of Search .................. 546/201, 273; 424/263, 424/267

[56] References Cited

U.S. PATENT DOCUMENTS 3,325,499  6/1967  Poos .................. 546/201

*Primary Examiner*—Richard A. Schwartz
*Attorney, Agent, or Firm*—Hammond & Littell, Weissenberger and Muserlian

[57] ABSTRACT

Novel 2H-indole-2-ones of the formula

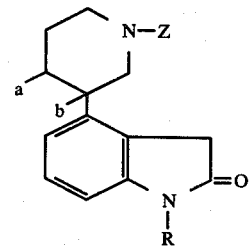

I wherein R is selected from the group consisting of hydrogen, alkyl of 1 to 8 carbon atoms and aralkyl of 7 to 12 carbon atoms, a and b are both hydrogen or together form a carbon-carbon bond, Z is selected from the group consisting of hydrogen, alkyl of 1 to 8 carbon atoms, hydroxyalkyl of 2 to 8 carbon atoms, aryloxyalkyl of 7 to 12 carbon atoms, cycloalkylalkyl of 4 to 12 carbon atoms, alkenyl and alkynyl of 3 to 8 carbon atoms and aralkyl of 7 to 12 carbon atoms optionally substituted with at least one member of the group consisting of halogen, alkoxy of 1 to 4 carbon atoms, alkyl of 1 to 4 carbon atoms, —OH, —CF$_3$, —OCF$_3$, —NO$_2$ and —NH$_2$ and their nontoxic, pharmaceutically acceptable acid addition salts having remarkable dopaminergic stimulating and antianoxic properties and their preparation.

15 Claims, No Drawings

DOPAMINERGIC STIMULATING AND ANTIANOXIC 4-SUBSTITUTED 2H-INDOLE-2-ONES

STATE OF THE ART

Chemistry of Heterocyclic Compounds, Indoles, Part 2, p. 142–143 describes the reactions of halo-indoles and copending, commonly assigned U.S. patent application Ser. No. 154,507 filed May 29, 1980, now U.S. Pat. No. 4,332,808 describes related indole compounds.

OBJECTS OF THE INVENTION

It is an object of the invention to provide the novel indoles of formula I and their non-toxic, pharmaceutically acceptable acid addition salts and their preparation.

It is another object of the invention to provide dopaminergic stimulating and antianoxic compositions and a novel method of inducing dopaminergic stimulating and antianoxic activity in warm-blooded animals.

These and other objects and advantages of the invention will become obvious from the following detailed description.

THE INVENTION

The novel compounds of the invention are selected from the group consisting of 2H-indole-2-ones of the formula

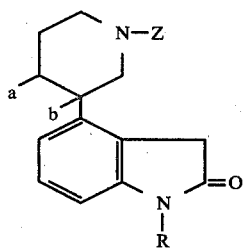

I wherein R is selected from the group consisting of hydrogen, alkyl of 1 to 8 carbon atoms and aralkyl of 7 to 12 carbon atoms, a and b are both hydrogen or together form a carbon-carbon bond, Z is selected from the group consisting of hydrogen, alkyl of 1 to 8 carbon atoms, hydroxyalkyl of 2 to 8 carbon atoms, aryloxyalkyl of 7 to 12 carbon atoms, cycloalkylalkyl of 4 to 12 carbon atoms, alkenyl and alkynyl of 3 to 8 carbon atoms and aralkyl of 7 to 12 carbon atoms optionally substituted with at least one member of the group consisting of halogen, alkoxy of 1 to 4 carbon atoms, alkyl of 1 to 4 carbon atoms, —OH, —CF$_3$, —OCF$_3$, —NO$_2$ and —NH$_2$ and their non-toxic, pharmaceutically acceptable acid addition salts.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid, aryl sulfonic acids such as benzene sulfonic acid and arylcarboxylic acids.

Examples of R are hydrogen, alkyl such as methyl, ethyl, propyl, isopropyl, butyl, isobutyl and pentyl are aralkyl such as benzyl and phenethyl. Examples of Z are hydrogen, alkyl such as methyl, ethyl, n-propyl, isopropyl, n-butyl, isobutyl, n-pentyl and n-hexyl; hydroxyalkyl such as hydroxyethyl, hydroxy-n-propyl, hydroxyisopropyl, hydroxy-n-butyl, hydroxy-isobutyl, hydroxy-n-hexyl and hydroxy-n-pentyl; aryloxyalkyl such as phenoxyethyl or phenoxypropyl; cycloalkylalkyl such as cyclopropylmethyl, cyclopropylethyl or cyclopropyl-n-propyl; alkenyl such as allyl; alkynyl such as propargyl; aralkyl such as benzyl or phenethyl optionally substituted with at least one member of the group consisting of halogen like chlorine or bromine, alkoxy like methoxy or ethoxy;, alkyl such as methyl, or ethyl, —OH, —CF$_3$, —OCF$_3$, —NO$_2$ and —NH$_2$.

Among the preferred compounds of formula I of the invention are those wherein R is hydrogen or alkyl of 1 to 8 carbon atoms and those wherein Z is hydrogen or alkyl of 1 to 8 carbon atoms and their acid addition salts. Specific preferred compounds of the invention are 1,3-dihydro-4-(1-propyl-1,2,5,6-tetrahydro-pyridin-3-yl)-2H-indole-2-one and 1,3-dihydro-4-(piperidin-3-yl)-2H-indole-2-one and their non-toxic, pharmaceutically acceptable acid addition salts.

The novel process of the invention for the preparation of a compound of formula I comprises subjecting a compound of the formula

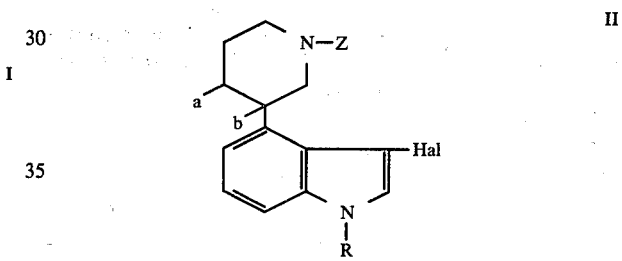

II wherein a,b,R and Z have the above definitions and Hal is chlorine or bromine to hydrolysis to obtain the corresponding compound of formula I which may be salified, if desired.

The hydrolysis of the compound of formula II is preferably effected with an aqueous mineral acid such as phosphoric acid, sulfuric acid and preferably hydrochloric acid. The aqueous acid solution may be concentrated but is preferably dilute such as N/10 hydrochloric acid.

A variation of the process of the invention comprises hydrolyzing a compound of the formula

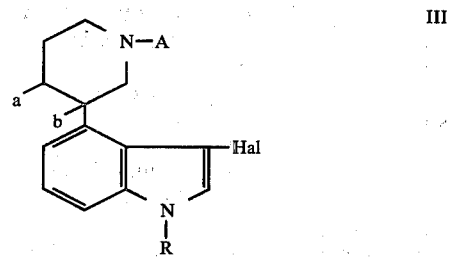

III wherein Hal, R, a and b have the above definitions and A is selected from the group consisting of hydrogen, benzyl and a protective group removable by acid hydrolysis to obtain a compound of the formula

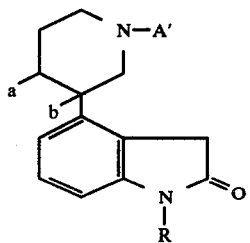

wherein R, a and b have the above definitions and A' is hydrogen or benzyl and optionally reacting the compound of formula $I_A$ wherein A' is benzyl with an agent to remove benzyl to obtain a compound of the formula

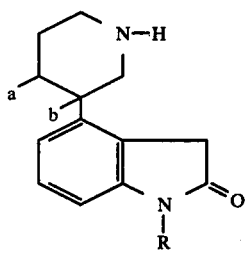

and reacting the latter with an agent capable of introducing Z' wherein Z' is Z other than hydrogen to obtain a compound of the formula

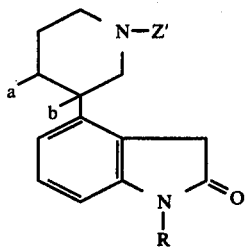

and optionally salifying the compounds of formula $I_A$, $I_B$ and $I_C$.

The hydrolysis of the compounds of formula III is preferably effected under the same conditions as the compounds of formula II. If a and b not form a carbon-carbon bond, the agent to remove benzyl on the piperidinyl nitrogen atom is preferably hydrogen in the presence of a catalyst such as palladium. If a and b do form a carbon-carbon bond, it is preferable to react the compound of formula $I_A$ with ethyl chloroformate to form the corresponding ethyl carbamate which is then hydrolyzed in an alkaline medium. The Z' radical may be introduced by reacting the compound of formula $I_B$ with a halide of the formula Z'-Hal' wherein Hal' is chlorine, bromine or iodine.

The compounds of formula I have a basic character and the acid addition salts thereof may be formed by reacting approximately stoichiometric amounts of the base and a mineral or organic acid with or without isolating the free base.

The novel dopminergic stimulating and antianoxic stimulating compositions of the invention are comprised of a dopaminergic stimulating and antianoxically effective amount of at least one compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions formed in the usual manner.

Examples of suitable excipients are lactose, starch, talc, arabic gum, magnesium stearate, cacao butter, aqueous and nonaqueous vehicles, fatty bodies of animal or vegetable origin, paraffinic derivatives, glycols, diverse wetting agents, dispersants or emulsifiers and preservatives.

Among the preferred compositions of the invention are those wherein R is hydrogen or alkyl of 1 to 8 carbon atoms and those wherein Z is hydrogen or alkyl of 1 to 8 carbon atoms and their acid addition salts. Specific preferred compounds of the invention are 1,3-dihydro-4-(1-propyl-1,2,5,6-tetrahydro-pyridin-3-yl)-2H-indole-2-one and 1,3-dihydro-4-(piperidin-3-yl)-2H-indole-2-one and their non-toxic, pharmaceutically acceptable acid addition salts.

The compositions of the invention are useful for the treatment of a large number of diseases of diverse pathological disorders such as the treatment of hypersecretion of prolactin by antehypophysis, the treatment of hypogonadism in males and females, as well as for the treatment of neurological syndromes of extrapyramidal origin such as the treatment of Parkinson disease and treatment of post-encephalitic parkinson syndromes. They are also useful for the treatment of cerebral senescence and geriatry.

The novel method of the invention of inducing dopaminergic stimulating and antianoxic activity in warm-blooded animals including humans, comprises administering to warm-blooded animals a dopaminergic stimulating and antianoxically effective amount of at least one compound of formula I and their non-toxic, pharmaceutically acceptable acid addition salts. The compounds may be administered orally rectally, or parenterally and the usual daily dose depends on the specific compound and the condition being treated. For example, the compound of Example 1 is administered orally at a daily dose of 0,075 to 1,5 mg/kg to treat a person for Parkinson disease.

The compounds of formula II and III are known or may be prepared by the process of French patent No. 2,458,549 and European patent application Ser. No. 0021,924.

In the following examples thare are described several preferred embodiments to illustrate the invention. However, it should be understood that the invention is not intended to be limited to the specific embodiments.

EXAMPLE 1

1,3-dihydro-4-(1-propyl-1,2,5,6-tetrahydro-pyridin-3-yl)-2H-indole-2-one hydrochloride STEP A: 3-bromo-4-(1-propyl-1,2,5,6-tetrahydro-pyridin-3-yl)-1H-indole A mixture of 9 g of 4-(1-propyl-1,2,5,6-tetrahydropyridin-4-yl)-1H-indole, 150 ml of dioxane and 7 g of N-bromosuccinimide was stirred for 3 hours under an inert atmosphere and was then diluted with water. The mixture was extracted with ethyl acetate and the organic phase was washed with water, with aqueous saturated sodium chloride solution, dried and evaporated to dryness at 40° C. under reduced pressure. The residue was chromatographed over silica gel and was eluted with a 6-3-1 cyclohexane-chloroform-triethylamine mixture to recover the fractions with an Rf=0.2. The said fractions were evaporated to dryness under reduced pressure and the residue was taken up in isopropyl ether. The mixture was filtered and the product was dried under reduced pressure to obtain 5.5 g of 3-bromo-4-(1-propyl-1,2,5,6-tetrahydro-pyridin-3-yl)-1H-indole melting at 156° C.

Analysis: $C_{16}H_{19}BrN_2$; molecular weight=319.251
Calculated: %C 60.20, %H 6.00, %N 8.77, %Br 25.03.
Found: 60.4, 6.0, 8.7, 25.0.

STEP B: 1,3-dihydro-4-(1-propyl-1,2,5,6-tetrahydropyridin-3-yl)-2H-indole-2-one hydrochloride A mixture of 5 g of the product of Step A in 100 ml of aqueous N hydrochloric acid was stirred for 3 hours and was then diluted with water. The mixture was made alkaline with with the addition of aqueous sodium hydroxide solution until the pH was basic and was then salted out with potassium carbonate. The mixture was extracted with ethyl acetate and the organic phase was evaporated to dryness to obtain 4.1 g of 1,3-dihydro-4-(1-propyl-1,2,5,6-tetrahydro-pyridin-4-yl)-1H-indole. The latter was dissolved in 100 ml of ethyl acetate and a solution of hydrogen chloride in ethyl acetate was added to the solution until the pH was acidic. The mixture was filtered and the product was washed with ethyl acetate and dried under reduced pressure to obtain 4.5 g of 1,3-dihydro-4-(1-propyl-1,2,5,6-tetrahydro-pyridin-3-yl)-2H-indole-2-one hydrochloride melting at 264° C. A sample was crystallized from a 2-1 isopropanol-methanol mixture for analysis.

Analysis: $C_{16}H_{20}N_2O$; molecular weight=292.810
Calculated: %C 65.63, %H 7.23, %N 9.57, %Cl 12.11.
Found: 65.4, 7.3, 9.3, 11.9.

EXAMPLE 2

1,3-dihydro-4-(piperidin-3-yl)-2H-indole-2-one

STEP A: 4-(1-trifluoroacetyl-piperidin-3-yl)-1H-indole 24.3 ml of trifluoroacetic acid anhydride were added at 0° to 10° C. to a mixture of 7 g of 4-(piperidin-3-yl)-1H-indole, 70 ml of chloroform and 48.6 ml of triethylamine and the mixture was stirred for 30 minutes and was diluted with water. The organic phase was decanted and the aqueous phase was extracted with chloroform. The combined organic phases were evaporated to dryness and the residue was chromatographed over silica gel. Elution with a 6-3-1 cyclohexane-chloroform-triethylamine mixture yielded 9.2 g of 4-(1-trifluoroacetylpiperidin-3-yl)-1H-indole melting at 170° C.

STEP B: 3-chloro-4-(1-trifluoroacetyl-piperidin-3-yl)-1H-indole

A mixture of 10 g of the product of Step A, 300 ml of dioxane and 5 g of N-chlorosuccinimide was stirred at 20° C. for 20 hours and was then diluted with water. The mixture was extracted with ethyl acetate and the organic phase was washed with water and aqueous sodium chloride solution, was dried and evaporated to dryness. The residue was chromatographed over silica gel and was eluted with a 6-3-1 cyclohexane-chloroform-triethylamine mixture to obtain 11 g of 3-chloro-4-(1-trifluoroacetyl-piperidin-3-yl)-1H-indole which was used as is for the next step.

STEP C: 1,3-dihydro-4-(piperidin-3-yl)-2H-indole-2-one hydrochloride

A mixture of 11 g of the product of Step B and 600 ml of N hydrochloric acid was refluxed for 3 hours and was then cooled to 20°-25° C. Concentrated sodium hydroxide was added to the mixture to make it alkaline and the mixture was then saturated with potassium carbonate. The mixture was extracted with ethyl acetate and the organic phase was dried and evaporated to dryness. The 3.65 g of residue were chromatographed over silica gel and eluted with a 7-2-1 chloroform-methanol-triethylamine mixture to obtain 3.6 g of 1,3-dihydro-4-(piperidin-3-yl)-2H-indole-2-one.

The said product was dissolved in 50 ml of ethyl acetate and 50 ml of isopropanol and then a solution of ethyl acetate saturated with hydrogen chloride was added thereto. The salt formed was dissolved in 300 ml of isopropanol and 100 ml of methanol and the solutions was refluxed and filtered hot. The filtrate was concentrated to a volume of 100 ml, was cooled and vacuum filtered. The recovered crystals were dried to obtain 3.6 g of 1,3-dihydro-4-(piperidin-3-yl)-2H-indole-2-one hydrochloride melting at >260° C.

Analysis: $C_{13}H_{17}Cl\ N_2O$; molecular weight at=252.745 Calculated: %C 61.78, %H 6.78, %N 11.08, %Cl 14,03. Found: 61.5, 6.9, 10.9, 14.0.

EXAMPLE 3

1,3-dihydro-4-(1-propyl-piperidin-3-yl)-2H-indole-2-one hydrochloride 1,3-dihydro-4-(piperidin-3-yl)-2H-indole-2-one and n-propyl iodide in dimethylformaimide were reacted in the presence of sodium carbonate to obtain 1,3-dihydro-4-(1-propyl-piperidin-3-yl)-2H-indole-2-one. A solution of the latter in ether was admixed with an ether solution saturated with hydrogen chloride and the recovered product after crystallization from an isopropanol-methanol mixture melted at 260° C.

EXAMPLE 4

1,3-dihydro-4-(1-methyl-piperidin-3-yl)-2H-indole-2-one

Using the procedure of Example 3, 1,3-dihydro-4-(piperidin-3-yl)-2H-indole-2-one and methyl iodide were reacted to obtain 1,3-dihydro-4-(1-methyl-piperidin-3-yl)-2H-indole-2-one which melted at 160° C. after crystallization from benzene.

EXAMPLE 5

Tablets were prepared containing 10 mg of 1,3-dihydro-4-(1-propyl-1,2,5,6-tetrahydro-piperidin-3-yl)-2H-indole-2-one and sufficient excipient of lactose, starch, talc and magnesium stearate for a final tablet weight of 100 mg.

PHARMACOLOGICAL STUDY

A. Rotation after unilateral lesion of nigrostriatal faisceau with 6-hydroxydopamine The lesion was effected on male rats weighing about 220 g by a unilateral injection of 8 μg of a 2 μg/μl solution of 6-hydroxydopamine into the nigrostriatal dopaminergic faisceau [Ungerstedt, Acta Physiol. Scand., Vol. 82, sup. 367 (1971) p. 69–93]. In these animals, the administration of direct dopaminergic agonists such as apomorphine by a general route such as intraveinously or intraperitoneally cause a rotation in the contralateral direction of the lesion side. The test compound was administered at least 5 weeks after the lesion and the animals were placed in an automatic rotometer to count the number of rotations effected by each animal in the 2 directions. The compound of Example 1 administered intraperitoneally at a dose of 2 mg/kg provoked 400 to 700 contralateral rotations per animal.

B. Inhibition of in vivo plasmatic prolactin

Pairs of male rats of the Sprague-Dawley strain were placed in cages and were left one week in a soundproof room at a controlled temperature of 22°±2° C. with 14 hours of artificial light and 10 hours of night. While anesthesized, a catheter was placed in the right superior vena cava of the rats and 48 hours later, the rats received intraperitoneally 5 mg/kg of reserpine and then orally 5 mg/kg of the test compound. The plasmatic prolactin was measured by the radioimmunological method of Euvrard et al [Neuropharmacology, Vol. 19 (1980), p. 379] in 0.7 ml blood samples. The results expressed in the duration of inhibition of plasmatic prolactin showed that the product of Example 2 inhibited plasmatic prolactin for about 20 hours.

C. Inhibition of prolactin secretion in rat cells in vitro

Primary cultures of anterior pituitary cells of rats were prepared by the technique of Drouin et al [Endocrinology, Vol. 98 (1976), p. 1528] and after incubation for 4 hours with the test product or without (controls), the prolactin present in the medium was measured by the radio-immonological method of Euvrard et al described in test B. The $DE_{50}$ which is the dose which inhibited by 50% the prolactin secretion as compared to the controls was 2 nmoles for the compound of Example 2 which shows that the said product inhibits the prolactin production.

D. Hyprobar anoxia in mice

Groups of 10 male mice weighing between 20 and 22 g were fasted for 5 hours and the time of survival was determined for the mice when placed in a hermetic enclosure in which the pressure was 90 mm Hg with the aid of a pump. The test compound was orally administered to the mice 30 minutes before the test and the controls received nothing. The results were expressed as the increase of the survival time as a percentage of the controls and was 50% and 5% at a dose of 10 and B 2 mg/kg, respectively of Example 1.

E. Acute toxicity

The $DL_0$ dose is the maximum dose at which no mice died after 8 days when the compounds of Examples 1 and 2 were orally administered to mice. The $DL_0$ for the compound of Example 1 was 200 mg/kg and was greater than 400 mg/kg for the compound of Example 2.

Various modifications of the compounds and methods of the invention may be made without departing from the spirit or scope thereof and it is to be understood that the invention is intended to be limited only as defined in the appended claims.

What we claim is:

1. A compound selected from the group consisting of 2H-indole-2-ones of the formula

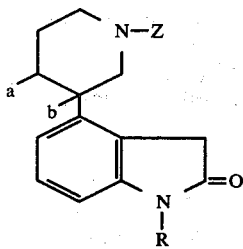

wherein R is selected from the group consisting of hydrogen, alkyl of 1 to 8 carbon atoms and aralkyl of 7 to 12 carbon atoms, a and b are both hydrogen or together form a carbon-carbon bond, Z is selected from the group consisting of hydrogen, alkyl of 1 to 8 carbon atoms, hydroxyalkyl of 2 to 8 carbon atoms, aryloxyalkyl of 7 to 12 carbon atoms, cycloalkylalkyl of 4 to 12 carbon atoms, alkenyl and alkynyl of 3 to 8 carbon atoms and aralkyl of 7 to 12 carbon atoms optionally substituted with at least one member of the group consisting of halogen, alkoxy of 1 to 4 carbon atoms, alkyl of 1 to 4 carbon atoms, —OH, —CF$_3$, —OCF$_3$, —NO$_2$ and —NH$_2$ and their non-toxic, pharmaceutically acceptable acid addition salts.

2. A compound of claim 1 wherein R is selected from the group consisting of hydrogen and alkyl of 1 to 8 carbon atoms.

3. A compound of claim 1 or 2 wherein Z is selected from the group consisting of hydrogen and alkyl of 1 to 8 carbon atoms.

4. A compound of claim 1 selected from the group consisting of 1,3-dihydro-4-(1-propyl-1,2,5,6-tetrahydropyridin-3-yl)-2H-indole-2-one and its non-toxic, pharmaceutically acceptable acid addition salts.

5. A compound of claim 1 selected from the group consisting of 1,3-dihydro-4-(piperidin-3-yl)-2H-indole-2-one and its non-toxic, pharmaceutically acceptable acid addition salts.

6. A dopaminergic stimulating and antianoxic composition comprising a dopaminergic stimulating and antianoxically effective amount of at least one compound of claim 1 and a pharmaceutical carrier.

7. A composition of claim 6 wherein in the compound R is selected from the group consisting of hydrogen and alkyl of 1 to 8 carbon atoms.

8. A composition of claim 6 or 7 wherein in the compound Z is selected from the group consisting of hydrogen and alkyl of 1 to 8 carbon atoms.

9. A composition of claim 6 wherein the active compound is selected from the group consisting of 1,3-dihydro-4-(1-propyl-1,2,5,6-tetrahydropyridin-3-yl)-2H-indole-2-one and its non-toxic, pharmaceutically acceptable acid addition salts.

10. A composition of claim 6 wherein the active compound is selected from the group consisting of 1,3-dihydro-4-(piperidin-3-yl)-2H-indole-2-one and its non-toxic, pharmaceutically acceptable acid addition salts.

11. A method of inducing dopaminergic stimulating and antianoxic activity in warm-blooded animals comprising administering to warm-blooded animals a dopaminergic stimulating and antianoxically effective amount of at least one compound of claim 1.

12. A method of claim 11 wherein in the compound R is selected from the group consisting of hydrogen and alkyl of 1 to 8 carbon atoms.

13. A method of claim 11 wherein in the compound Z is selected from the group consisting of hydrogen and alkyl of 1 to 8 carbon atoms.

14. A method of claim 11 wherein the active compound is selected from the group consisting of 1,3-dihydro-4-(1-propyl-1,2,5,6-tetrahydropyridin-3-yl)-2H-indole-2-one and its non-toxic, pharmaceutically acceptable acid addition salts.

15. A method of claim 11 wherein the active compound is selected from the group consisting of 1,3-dihydro-4-(piperidin-3-yl)-2H-indole-2-one and its non-toxic, pharmaceutically acceptable acid addition salts.

* * * * *